United States Patent [19]

Dyke

[11] 4,003,382
[45] Jan. 18, 1977

[54] RETENTION CATHETER AND METHOD OF MANUFACTURE
[75] Inventor: Denis G. Dyke, Fords, N.J.
[73] Assignee: Ethicon, Inc., Somerville, N.J.
[22] Filed: July 25, 1975
[21] Appl. No.: 599,293
[52] U.S. Cl. .......................................... 128/349 B
[51] Int. Cl.² ...................................... A61M 25/00
[58] Field of Search ........ 128/348, 349 B, 349 BV, 128/350 R, 351, 246, 325, 344

[56] References Cited
UNITED STATES PATENTS

| | | |
|---|---|---|
| 3,292,627 | 12/1966 | Harautuneian ................ 128/349 B |
| 3,528,869 | 9/1970 | Dereniuk .................... 128/349 B X |
| 3,850,720 | 11/1974 | Collins .............................. 156/155 |

Primary Examiner—Dalton L. Truluck
Attorney, Agent, or Firm—Wayne R. Eberhardt

[57] ABSTRACT

An all plastic retention catheter of the Foley type having a body of a thermoplastic polyurethane and a balloon of a thermosetting polyurethane. The catheter may be fabricated by a method wherein the thermosetting polyurethane balloon sleeve is molded with integral bands of a thermoplastic polyurethane polymer spaced at either end of the sleeve and subsequently sealed to the catheter body by fusing the thermoplastic bands to the body material with heat or solvent.

11 Claims, 7 Drawing Figures

RETENTION CATHETER AND METHOD OF MANUFACTURE

BACKGROUND OF THE INVENTION

1. Field of the Invention

This invention relates to balloon or Foley type retention catheters. More particularly this invention relates to an all plastic catheter having a thermosetting polyurethane balloon, and further to a method for sealing the balloon to a thermoplastic polyurethane catheter body.

2. Description of Prior Art

Retention type catheters have been in use for many years and traditionally comprise a flexible and resilient tubular body portion having elongated drainage and inflating lumens extending longitudinally therethrough. An opening is provided in the catheter wall extending into communication with the inflating lumen and an inflatable sack or balloon is secured to the catheter over the opening whereupon introduction of fluid pressure through the inflating lumen will cause the sack or balloon to distend. The distal end of the catheter adapted for insertion into the patient is normally closed off and rounded and drainage eyes are provided in the catheter wall in communication with the drainage lumen, said eyes being located intermediate the balloon and the catheter distal end. At the opposite proximal end of the catheter, funnel portions are provided in communication with the inflating and drainage lumens, respectively, the tubular body normally being bifurcated adjacent its proximal end, whereupon the proximal ends of the inflating ends drainage lumen extend angularly from each other. Catheters of this general type are illustrated in U.S. Pat. Nos. 2,248,934 and 2,308,404.

Although catheters of the general type described supra have been conventionally made of rubber, recent developments have been directed toward the fabrication of all plastic catheters which reportedly show less tendency for the formation of undesirable calcium or other salts in the drainage lumen, and which have a high degree of biocompatibility. Such all-plastic catheters are described for example in U.S. Pat. Nos. 3,392,627, 3,528,869 and 3,539,674.

Typical plastic materials which have been utilized in the fabrication of catheters include polyurethane, polyvinyl chloride and copolymers of vinyl chloride with vinyl acetate or ethylene. Particularly preferred compositions for catheter bodies are the elastomeric grades of polyurethane such as Estane polyester-polyurethane of the B. F. Goodrich Chemical Company. Balloons of thermoplastic polyurethanes however, have been found to require higher inflation pressures than conventional latex balloons and to take a permanent set after prolonged inflation possibly causing trauma to the patient upon withdrawal. As a result, it has been suggested to use latex balloons with polyurethane catheter bodies as in U.S. Pat. Nos. 3,112,748 and 3,850,720. In such constructions the latex balloons may be Teflon-coated to render them less irritating to the patient while largely preserving the desirable balloon inflation/deflation properties of latex. Even Teflon coating, however, does not completely eliminate tissue reaction to the latex material.

It is accordingly an object of the present invention to provide an all plastic catheter having improved inflation/deflation properties. It is a further object of this invention to provide an all plastic catheter having a thermosetting polyurethane balloon member. A yet further object of this invention is to provide a method for securely attaching a thermosetting polyurethane balloon to a thermoplastic polyurethane catheter body. Yet other objects of the invention will be apparent from the ensuing descriptions and examples.

SUMMARY

A Foley type retention catheter is constructed having a thermoplastic polyurethane body member and a thermosetting polyurethane balloon member. In one method of assembly, the balloon member is cast over a mandrel previously covered at each end with bands of thermoplastic polyurethane polymer corresponding to the areas of the balloons to be sealed to the catheter tube. The thermoplastic polyurethane bands bond to the thermosetting polyurethane balloon material at the interface between the materials during curing of the balloon material. The balloon is subsequently sealed to the catheter body by uniting these thermoplastic polyurethane bands to the thermoplastic polyurethane catheter body with heat or solvent.

DESCRIPTION OF PREFERRED EMBODIMENTS

Figure 1:
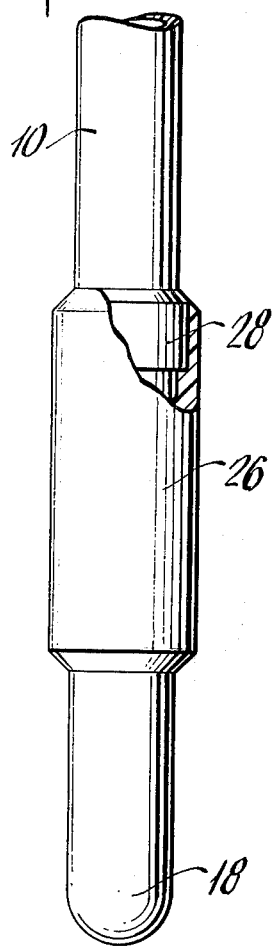
FIG. 1 is an elevational view with parts broken away and sectioned of the distal end of a Foley catheter having a thermosetting polyurethane balloon mounted over a thermoplastic polyurethane catheter body.
Figure 2:
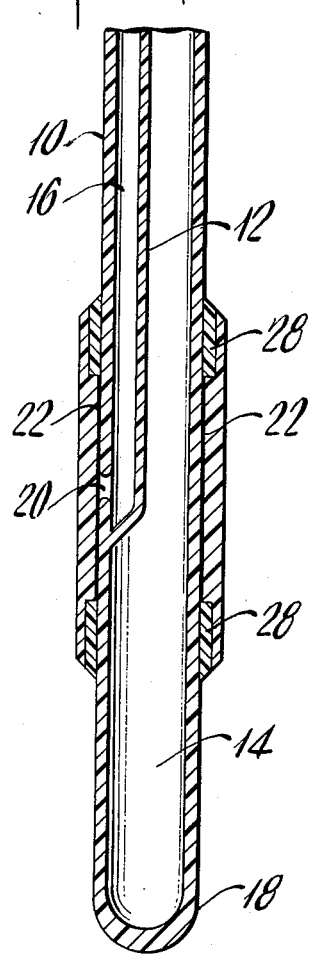
FIG. 2 is an elevational view with part sectioned for clarity of the catheter body and the balloon of FIG. 1.
Figure 3:
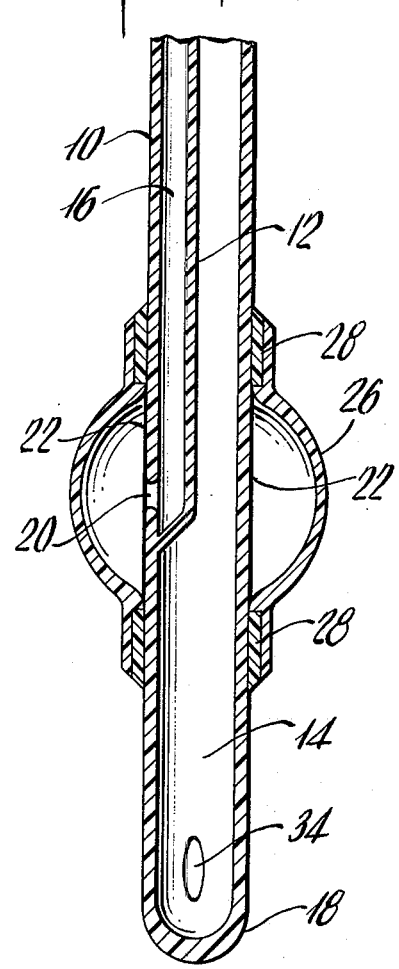
FIG. 3 shows the same assembly as FIG. 2 with the balloon thereof inflated.

The catheter bodies for use in the present invention may be fabricated in accordance with conventional procedures. In one typical procedure, manufacturing begins with the formation of a plastic catheter shaft, usually by extrusion, to form cylindrical tube 10 having a longitudinal internal partition 12 which divides the interior of the catheter shaft 10 into a drainage lumen 14 and an inflation lumen 16 as illustrated in FIGS. 1-3. The extrusion process produces an open ended cylindrical tube and the distal tip 18 of the catheter shaft 10 is rounded and closed off by means of a conventional heat molding. An inflation port 20 is punched into the wall of the catheter shaft 10 near the distal end of the catheter and in communication with the inflation lumen 16. This step must be done before the inflation balloon is attached since the inflation port 20 must ultimately be within the balloon.

As an optional final step in the preparation of the catheter shaft, a coating of release agent 22 may be applied circumferentially about the catheter shaft 10 in the neighborhood of the inflation port 20 and for a short distance above and below the port. The purpose of such coating is to provide good separation between the catheter shaft 10 and the balloon which is attached thereover at a later stage of the manufacturing process. Release agents such as siloxane or colloidal hydrated alumina are well known in the art and commonly employed in catheter manufacture.

The next step in the manufacturing process is to put a similar coating of a release agent, preferably siloxane, over cylindrical mandrel 24 of FIG. 4 so that the polyurethane sleeve which is ultimately to form the inflation balloon can be preformed upon mandrel 24 and later easily removed therefrom.

The catheter body is preferably fabricated of thermoplastic polyurethane, and the dissimilarity between the thermoplastic polyurethane body and the thermosetting polyurethane balloon makes it difficult to provide a strong adhesive bond between the two materials. Whereas catheters of the prior art constructed entirely of thermoplastic polyurethanes are conveniently assembled by fusing as described for example in U.S. Pat. No. 3,528,869, such heat sealing is ineffective between the thermoplastic and thermosetting polyurethanes. This problem of sealing the balloon to the catheter shaft is avoided by a method wherein thermoplastic polyurethane bands are integrally molded within the thermosetting polyurethane sleeve to provide a composite balloon sleeve with a heat sealable area at each end. In the practice of this method, a good bond is achieved at the interface of the thermoplastic polyurethane bands and the thermosetting polyurethane body of the sleeve. While not wishing to be bound by theory, it is believed that while the uncured thermosetting balloon material is in contact with the thermoplastic urethane bands previously placed on the mandrel, the polymeric isocyanate in the balloon formulation cross-links with the surface of the thermoplastic polyurethane by allophanate and biuret bonds. After the balloon sleeve is cured, the exposed surfaces of the thermoplastic polyurethane bands which have not been influenced by the cross-linking can be made to flow and fuse to the thermoplastic polyurethane catheter body by application of heat or solvent.

Figure 4:
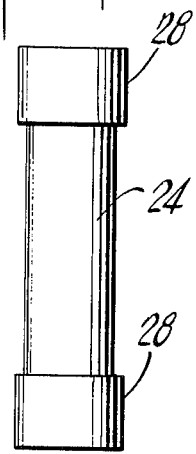
FIG. 4 is an elevational view of the balloon mandrel covered at each end with a band of thermoplastic polyurethane.

In a preferred embodiment, composite balloon sleeve 26 is preformed upon mandrel 24 by first covering each end of the mandrel with bands 28 of a thermoplastic polyurethane as illustrated in FIG. 4. The width of the bands corresponds to the desired seal area for the balloon. The bands may be cut from thin walled thermoplastic polyurethane tubing and slipped over the ends of the mandrel, or may be formed in place by coating the ends of the mandrel with a solution of a thermoplastic polyurethane. Suitable thermoplastic polyurethane solutions commercially available include Witcobond F-2, a product of Witco Chemical Corp., Chicago, Ill., and B. F. Goodrich Co.'s Estane brand of high molecular weight polyurethane material, such as Estane 5,740 × 101 (a moderately high modulus polyester type polyurethane), Estane 5,702 (a low modulus polyester type polyurethane), blends of these two, and Estane 5,740 × 140 (a moderately high modulus polyether type thermoplastic polyurethane). The polymer solutions can be applied to the mandrel by dipping or any other convenient method including spraying, transfer coating, wiping or brushing.

Figure 5:
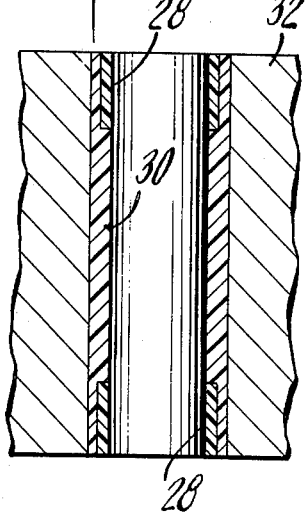
FIG. 5 is a cross-sectional view of the balloon mold with the mandrel in place and covered by a thermosetting polyurethane balloon material.
Figure 6:
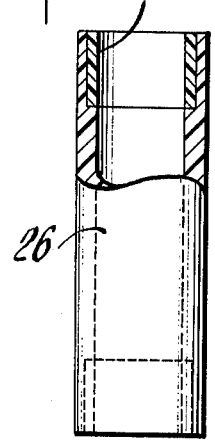
FIG. 6 is an elevational view with parts broken away and sectioned of the plastic balloon molded according to FIG. 5.
Figure 7:
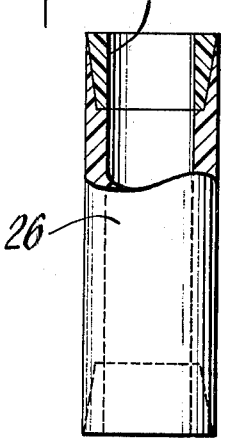
FIG. 7 is an elevational view with parts broken away and sectioned of an alternate balloon construction showing a thermosetting polyurethane band having a decreasing thickness.

After the ends of the mandrel have been covered with the thermoplastic polyurethane, the mandrel is centered in mold 32 which is then charged with an amount of thermosetting polyurethane resin 30 sufficient to fill the mold with the mandrel positioned therein as shown in FIG. 5. Resin 30 is cured in the mold to form a solid polyurethane sleeve having a wall thickness of from about 6 to 20 thousandths of an inch. The sleeve is subsequently removed from the mold and stripped from the mandrel to obtain the composite structure shown in FIG. 6, a balloon sleeve 26 having a thermosetting polyurethane body 30 with integral bands of thermoplastic polyurethane molded within the ends thereof.

Subsequently, as illustrated in FIG. 1, a sleeve 26 is slipped over catheter body 10 to surround the shaft in the neighborhood of the inflation port 20. Balloon sleeve 26 and catheter body 10 are preferably separated by a thin film of release agent 22 over that portion of the body between bands 28 at either end of sleeve 26.

Once in position, the sleeve 26 is permanently sealed to catheter body 10 by activating thermoplastic bands 28 with heat or solvent in order to fuse the bands to the catheter body. Heating may be accomplished by radio frequency, induction, dielectric or direct application through heated molds. One method employing heated molds is disclosed in U.S. Pat. No. 3,528,860, incorporated herein by reference. The mold comprises a pair of ring elements sized to match the diameter of the catheter at the balloon section and designed to surround the end portions of the sleeve. The inner surfaces of the rings may be outwardly tapered to a smaller diameter corresponding to the diameter of catheter body, the effect of the taper being to reduce the size of the ridge at the point where the balloon joins the catheter body. During the sealing operation, fluid pressure is introduced into the catheter body 10 through drainage lumen 14 to prevent the collapse of body 10 under the molding pressure. Alternatively, the seal may be accomplished by application of a solvent or additional thermoplastic polyurethane solution which acts as an adhesive for the thermoplastic polyurethane polymer.

After sealing the balloon to the catheter body, the catheter may be finished by smoothing the joint at the balloon by trimming or filling with a polyurethane polymer if necessary, and by cutting drainage eyes 34 through the wall of shaft 10 to communicate with drainage lumen 14.

Polymer 30 forming the body of balloon 26 is a thermosetting polyurethane having elongation and recovery properties which permit the catheter balloon to be readily inflated with low pressures and with a low order of permanent elongation set. Preferably, the balloon material has an elongation to break of more than 400 percent and an elongation set, i.e., residual increase in balloon circumference after deflation, of less than about 15 percent after remaining fully inflated in urine at 37° C for one week. Comparative data on specific properties of the thermosetting polyurethane balloons of the present invention and typical properties of other conventional catheter balloon materials are presented below.

| Balloon Material | Wall Thickness | Break Elongation | Elongation Set | Inflation Pressure |
| --- | --- | --- | --- | --- |
| Thermosetting polyurethane (A) | 15 mils | 535% | 5–11% | 4.1 psi |
| Thermosetting polyurethane (B) | 18 | 510 | 0–5 | 8.6 |
| Thermoplastic Pharmaseal polyurethane | 10–15 | 400–600 | 180–200 | 17 |
| Silicone rubber Travenol | 15–20 | 500–700 | 60–70 | 8.1 |
| Teflon coated latex (Kosan) | 15–20 | 500–800 | 30–40 | 7.9 |

In the above table, thermosetting polyurethane balloons A and B were each cast with integral bands of a thermoplastic polyurethane in the seal areas at each end of the balloon by precoating the ends of the balloon mandrel with a solution of Witcoband F-2 polymer. Thermosetting polyurethane (A) was formulated from Cyanaprene A9 polyester-polyurethane prepolymer (American Cyanamid Co.) cross-linked with an excess of a polyfunctional polyol and plasticized with approximately 18.5 percent dimethoxyethyl phthalate. Thermosetting polyurethane (B) was formulated from Solithane 790 urethane prepolymer (Thiokol Chemical Corp.) crosslinked with an excess of a polyfunctional polyol and unplasticized. Examples of suitable cross-linking agents include trimethylol propane, 1,4,-butanediol, mixtures of trimethylolpropane and triisopropanol amine, other primary and secondary trifunctional polyols. Examples of other suitable plasticizers include the dialkylene glycol dibenzoates. Any nontoxic cross-linking agent or plasticizer conventional for use in formulating thermosetting polyurethane resins may be used although the elongation and inflation characteristics are preferably separately determined for each individual formulation to assure that desirable properties of the thermosetting polyurethane are retained.

The method of fabricating the catheters of the present invention wherein a thermosetting polyurethane balloon component is provided with integral sections of thermoplastic polyurethane over the areas to be joined to a thermoplastic polyurethane tube component has applications beyond the fabrication of catheters. For example, in the medical field, the same method may be utilized to fabricate artificial heart valves or other prosthetic devices where a bicomponent construction of thermosetting and thermoplastic polyurethane is desired. The method of the present invention is accordingly not limited to the fabrication of catheters, but broadly encompasses a method of fabricating articles of thermosetting and thermoplastic polyurethane components which comprises contacting solid thermoplastic polyurethane with a thermosetting polyurethane resin, curing the thermosetting polyurethane resin while in contact with the thermoplastic polyurethane whereby bonding occurs between the surface of the thermoplastic polyurethane and the thermosetting polyurethane, and thereafter joining the thermosetting polyurethane component to the thermoplastic polyurethane component by fusing the thermoplastic polyurethane section of the thermosetting polyurethane component to the thermoplastic polyurethane component.

While the integral thermoplastic polyurethane bands are the preferred method for attaching the thermosetting polyurethane balloon sleeve to a thermoplastic lumen tube, a single component thermosetting polyurethane sleeve can be attached to a thermoplastic polyurethane catheter body through the use of a selected urethane or epoxy adhesive system. For example, a 40 percent solution of a polyester polyurethane prepolymer in methyl ethyl ketone containing about 0.8 percent by weight of a polymeric isocyanate cross-linking agent provides good bond strength between the thermoplastic and thermosetting polyurethanes when dried at 60° C for 24 hours and cured for 2 minutes at 120° C. Suitable cross-linking agents are the organic diisocyanates including aromatic, aliphatic and cycloaliphatic diisocyanates and combinations of these. Representative compounds include 1,4-tetramethylene diisocyanate, 1,6-hexamethylene diisocyanate, 1,4-cyclohexylene diisocyanate, and 4,4'-methylene-bis-(cyclohexyl isocyanate). While not wishing to be bound by theory, the adhesive mechanism of this system is believed to include hydrogen bonding and cross-linking of the polymeric isocyanate in allophanate and biuret bonding.

While thermoplastic polyurethane is the preferred material for the catheter body, other plastic materials such as polyvinyl chloride, polyvinylidene chloride, and silicone elastomers may be used with the thermosetting polyurethane balloon sleeve to obtain a biocompatible all plastic catheter having improved inflation/deflation properties. The plastic materials used in forming the catheters of the present invention may be pigmented or unpigmented. In some cases, pigments designed to give X-ray opacity may be incorporated in the material. In a preferred embodiment of the invention, a small amount of very finely divided white pigment, e.g., about 0.01 to 1 percent by weight of titanium dioxide pigment, is incorporated in the otherwise transparent material used in forming the catheter body to give the final extruded tube a milky translucency or opaque white appearance.

The catheters of the present invention may also include special features which are known in the construction of medicosurgical tubes and which may be required for particular procedures in which the catheters are to be employed. These may include a non-sparking feature (U.S. Pat. No. 3,070,132), X-ray line feature (U.S. Pat. No. 2,847,915) or a tapered section feature (U.S. Pat. No. 2,940,126).

Yet other variations in catheter compositions, construction and design will be apparent to those skilled in the art, and all such variations as applied to the catheters having a thermosetting polyurethane balloon member are included within the scope of the present invention.

What is claimed is:

1. A retention catheter comprising:

a. an elongated flexible thermoplastic tube having a distal end and a proximal end and having a drainage lumen and an inflation lumen defined by the walls of said tube and extending from said proximal end to near said distal end, said inflation lumen terminating in an inflation port in the wall of the tube near the distal end thereof, said drainage lumen terminating in a drainage port in the wall of the tube intermediate said inflation port and said distal end, and b. a cylindrical thermosetting polyurethane balloon sleeve encircling a longitudinal section of said tube containing said inflation port and having end margins sealed to said tube on either side of said inflation port.

2. A catheter of claim 1 wherein that portion of the balloon sleeve intermediate the end margins is substantially free from adhesion to said tube.

3. A catheter of claim 1 wherein said thermosetting polyurethane balloon sleeve is characterized by a break elongation in excess of 400 percent and an elongation set of less than about 15 percent.

4. A catheter of claim 1 wherein said tube is a thermoplastic polyurethane.

5. A catheter of claim 4 wherein said end margins of said balloon sleeve are adhesively sealed to said tube with a polyurethane-isocyanate adhesive.

6. A catheter of claim 1 wherein said tube is comprised of a material selected from the group consisting of polyvinyl chloride, polyvinylidene chloride and silicone elastomers.

7. A catheter of claim 1 wherein said tube is pigmented.

8. A catheter of claim 1 wherein said tube and said balloon are pigmented.

9. A catheter of claim 7 wherein said tube is pigmented with about 0.01 to 1% by weight of titanium dioxide.

10. A retention catheter comprising:
a. an elongated flexible thermoplastic polyurethane tube having a distal end and a proximal end and having a drainage lumen and an inflation lumen defined by the walls of said tube and extending from said proximal end to near said distal end, said inflation lumen terminating in an inflation port in the wall of the tube near the distal end thereof, said drainage lumen terminating in a drainage port in the wall of the tube intermediate said inflation port and said distal end, and b. a cylindrical thermosetting polyurethane balloon sleeve encircling a longitudinal section of said tube containing said inflation port and having end margins sealed to said tube on either side of said inflation port, said end margins comprising bands of thermoplastic polyurethane integral with the inner surface of the balloon sleeve.

11. A catheter of claim 10 wherein said thermosetting polyurethane balloon sleeve is characterized by a break elongation in excess of 400 percent and an elongation set of less than about 15%.

* * * * *